United States Patent
Itoh (10) Patent No.: US 7,159,489 B2
(45) Date of Patent: Jan. 9, 2007

(54) CAP REMOVING APPARATUS FOR REMOVING CAP FROM TUBE-LIKE CONTAINER

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 91 days.

(21) Appl. No.: 11/122,072

(22) Filed: May 5, 2005

(65) Prior Publication Data

US 2005/0252342 A1 Nov. 17, 2005

(30) Foreign Application Priority Data

May 14, 2004 (JP) .............................. 2004-144796

(51) Int. Cl.
*B67B 7/00* (2006.01)
*B67B 7/16* (2006.01)
*B65B 43/26* (2006.01)

(52) U.S. Cl. ........................................ 81/3.2; 53/381.4
(58) Field of Classification Search ................... 81/3.2, 81/3.36, 3.4, 3.55, 3.27; 53/381.4; 215/302, 215/3.5; 220/274
See application file for complete search history.

(56) References Cited

U.S. PATENT DOCUMENTS 4,982,553 A * 1/1991 Itoh ............................ 53/246
5,080,864 A * 1/1992 Shaw ........................... 422/62
5,481,946 A * 1/1996 Nishikawa et al. ........... 81/3.2
6,321,619 B1 * 11/2001 Itoh .............................. 81/3.2
2005/0047966 A1 * 3/2005 Itoh ............................. 422/99

FOREIGN PATENT DOCUMENTS

JP              2731729        * 12/1997

* cited by examiner

Primary Examiner—Joseph J. Hail, III
Assistant Examiner—Bryan R. Muller
(74) Attorney, Agent, or Firm—Nixon & Vanderhye P.C.

(57) ABSTRACT

An apparatus comprises a holder which holds a container blocked by a cap, and a transport path which has a correcting position. A rotation mechanism is provided at the correcting position. When the container is rotated by the rotation mechanism, a posture of a knob portion of the cap is corrected by a correction mechanism. The corrected knob portion is grasped by a removing mechanism. The removing mechanism removes the cap from the container. The correction mechanism can be moved between a first position at which the correction mechanism advances to the correcting position and a second position at which the correction mechanism retreats from the correcting position. The removing mechanism can be moved between a third position at which the removing mechanism advances to the correcting position and a fourth position. The removing mechanism is moved to the third position when the correction mechanism retreats to the second position.

9 Claims, 10 Drawing Sheets

CAP REMOVING APPARATUS FOR REMOVING CAP FROM TUBE-LIKE CONTAINER

CROSS-REFERENCE TO RELATED APPLICATIONS

This application is based upon and claims the benefit of priority from prior Japanese Patent Application No. 2004-144796, filed May 14, 2004, the entire contents of which are incorporated herein by reference.

BACKGROUND OF THE INVENTION

1. Field of the Invention

This invention relates to a cap removing apparatus employed when, for example, a cap blocking an opening of a test tube is removed from the test tube and, more particularly, to a structure to correct a posture of a knob portion provided on an outer peripheral edge of the cap to a regular posture and automatically remove the cap from the opening of the test tube by grasping the knob portion.

2. Description of the Related Art

For example, an opening of a test tube containing a sample such as blood is blocked by a cap. The cap is produced of a soft material such as synthetic resin and has a flange-like knob portion on an outer peripheral edge thereof. To remove this kind of cap from a test tube, the cap has been detached from an opening of the test tube by grasping the knob portion by fingertips. However, removing caps one by one from respective test tubes by manual work has spent much time and the operability has been poor.

Thus, a removing apparatus for automatically removing a cap from an opening of a test tube has been developed. Japanese Patent No. 2731729 discloses such a removing apparatus. The publicly known removing apparatus comprises a holder which holds a test tube in an upright posture, a transport path having a belt conveyor which transports the test tube held by the holder together with the holder, a rotation mechanism provided in the transport path to rotate the test tube about a central longitudinal axis thereof, a correction mechanism which corrects a posture of a knob portion of a cap when the test tube is rotated by the rotation mechanism, and a removing mechanism which removes the cap from the test tube by grasping the knob portion having the posture corrected by the correction mechanism.

The transport path of the removing apparatus has a correcting position and a removing position at its middle part. The correcting position and the removing position are separated from each other in a transporting direction of the test tube. The rotation mechanism and the correction mechanism are provided at the correcting position. The removing mechanism is provided at the removing position.

The test tube transported in the transport path is fed to the removing position via the belt conveyor after the posture and direction of the knob portion of the cap are corrected at the correcting position. The cap is removed from the opening of the test tube by the removing mechanism, at the removing position.

In the conventional removing apparatus, however, since the correction mechanism and the removing mechanism are separated from each other in the transporting direction of the test tube, the transport path is long. As a result, a large space to provide the transport path is required and the removing apparatus cannot be made compact.

Moreover, transmission of vibration from the belt conveyor to the test tube cannot be prevented during a process in which the test tube is transported from the correcting position to the removing position. Thus, the test tube is rotated little by little about a central longitudinal axis thereof and the direction of the knob portion corrected at the correcting position is changed. As a result, even if the test tube is fed to the removing position, the knob portion of the cap cannot be grasped by the removing mechanism. Therefore, the cap cannot be removed from the test tube or the operation of removing the cap cannot be automated.

In addition, the test tube is transported from the correcting position to the removing position every time the cap is removed from the test tube, in the conventional removing apparatus. For this reason, much time must be spent after correcting the knob portion of the cap and before removing the cap.

BRIEF SUMMARY OF THE INVENTION

The object of the present invention is to provide a cap removing apparatus in which correcting the knob portion of the cap and removing the cap can be successively conducted at the same correcting position.

According to an aspect of the present invention, there is provided a cap removing apparatus comprising a holder which holds a tube-like container having an opening blocked by a cap, the cap having a knob portion at an outer peripheral edge thereof, a transport path in which the container held by the holder is transported together with the holder, the transport path having a correcting position at a middle part thereof, a rotation mechanism provided at the correcting position to rotate the container about a central longitudinal axis thereof when the container is transported to the correcting position, a correction mechanism which corrects a posture of the knob portion of the cap when the container is being rotated by the rotation mechanism, and a removing mechanism which grasps the knob portion of the cap corrected by the correction mechanism and removes the cap from the container.

The correction mechanism is configured to move between a first position at which the correction mechanism advances to the correcting position to correct the posture of the knob portion and a second position at which the correction mechanism retreats from the correcting position.

The removing mechanism is configured to move between a third position at which the removing mechanism advances to the correcting position to remove the cap from the container and a fourth position at which the removing mechanism retreats from the correcting position.

The removing mechanism is moved to the third position when the correction mechanism retreats to the second position.

According to the present invention, correcting the knob portion and removing the cap after correction can be successively conducted at the same correcting position in the transport path. For this reason, the knob portion of the cap can be certainly grasped by the removing mechanism and quickly removed from the opening of the container. In addition, the container does not need to be moved along the transport path during the period after correction of the knob portion is ended and after removing the cap is completed. Therefore, the transport path can be shortened and the apparatus can be made compact.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be explained below with reference to the accompanying drawings.

Figure 1:
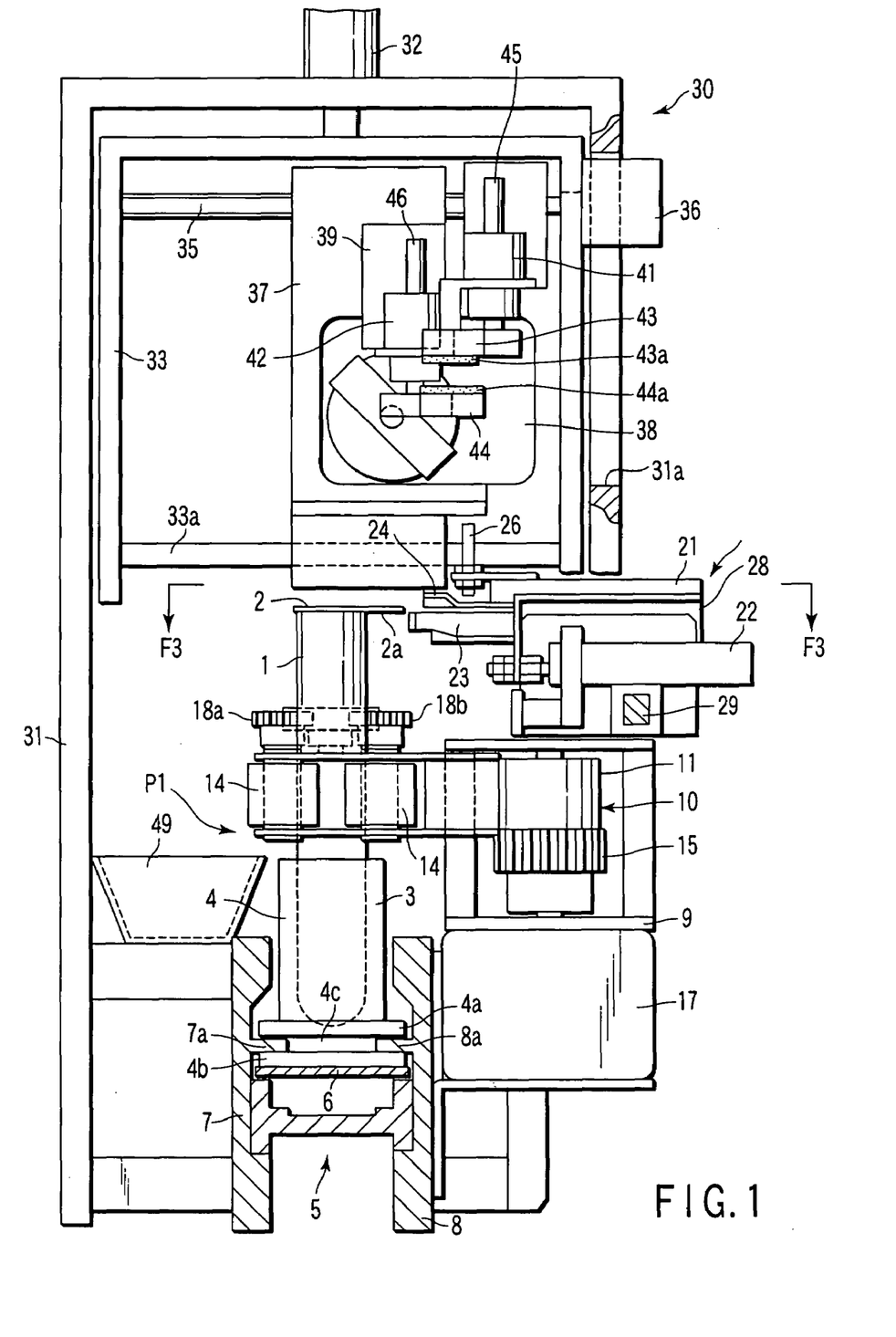
FIG. 1 is a front view of a cap removing apparatus according to an embodiment of the present invention.
Figure 2:
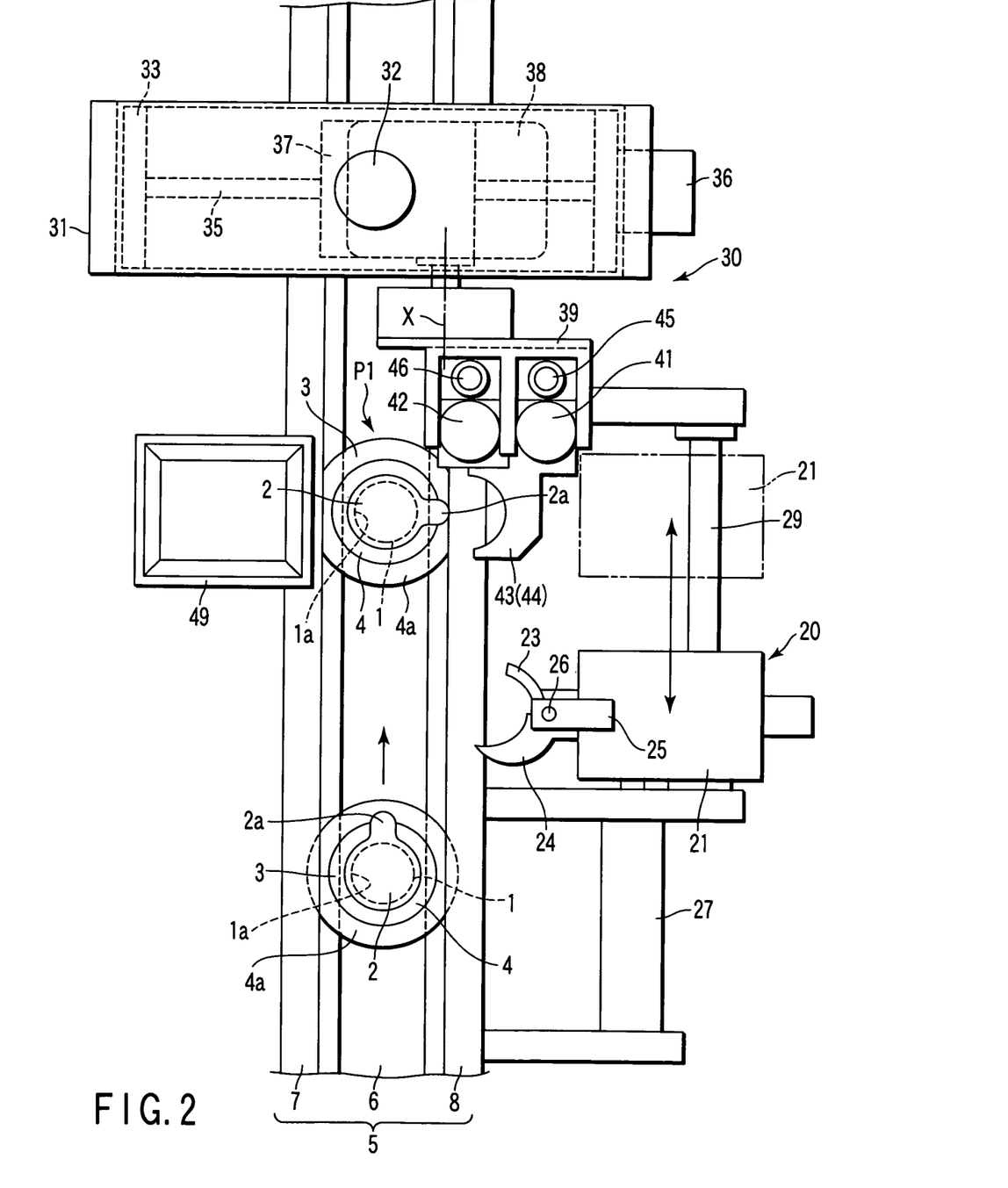
FIG. 2 is a plan view of the cap removing apparatus according to the embodiment of the present invention, showing a relationship in position among a transport path in which a test tube is transported, a correction mechanism which corrects a knob portion of a cap, and a removing mechanism which removes the cap from an opening of the test tube.
Figure 3:
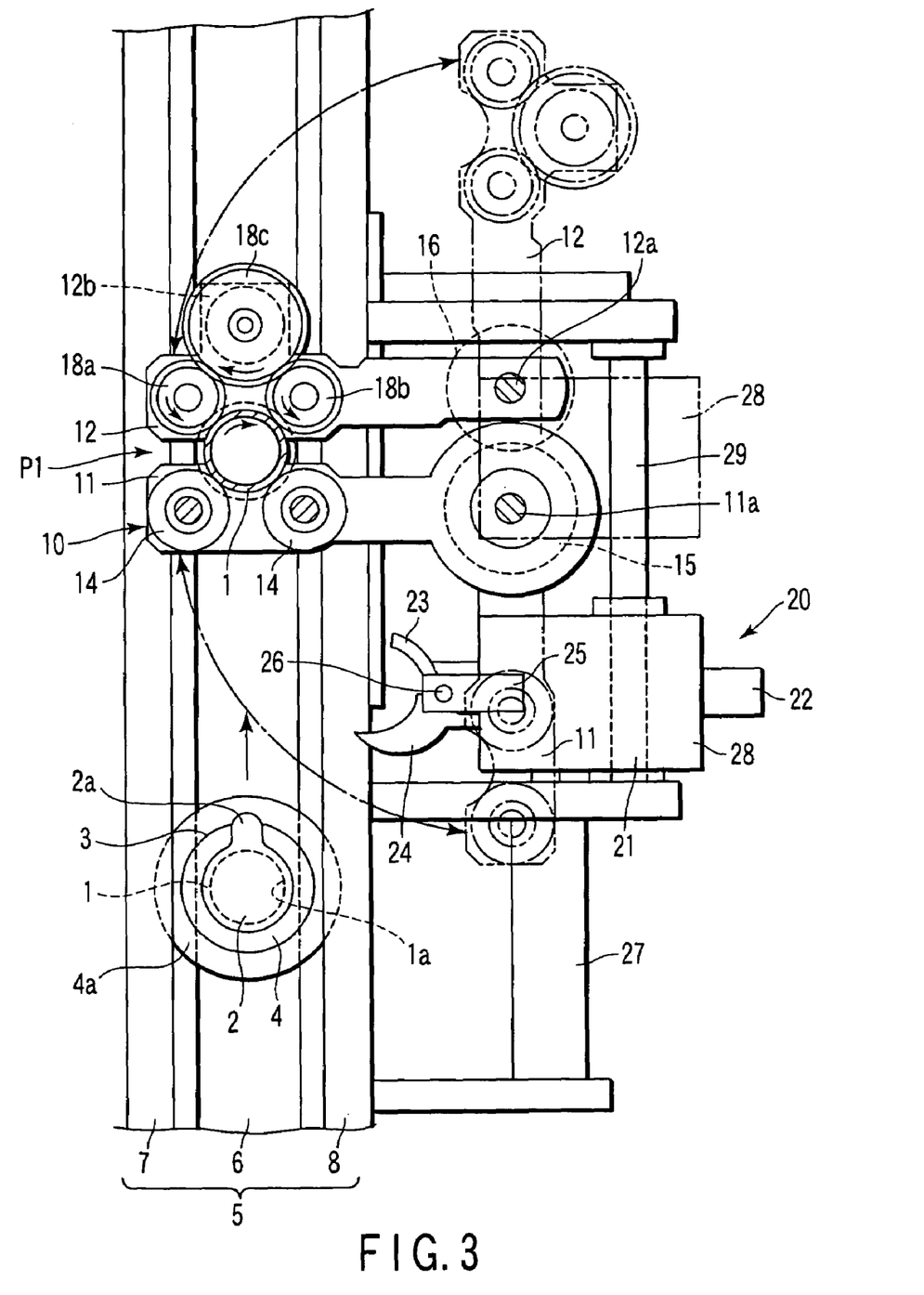
FIG. 3 is a cross-sectional view as seen along a line F3—F3 of FIG. 1.

FIG. 1 to FIG. 3 show a cap removing apparatus according to the embodiment of the present invention. The apparatus comprises a holder 3 which holds a test tube 1. The test tube 1 is a tube-like container and contains, for example, a sample such as blood. The test tube 1 has an opening 1a blocked by a cap 2. The cap 2 is shaped in disk and is produced of, for example, a flexible material such as resin. The cap 2 has a knob portion 2a. The knob portion 2a expands from an outer peripheral edge of the cap 2 in a radial direction of the cap 2.

The holder 3 has a tubular portion 4 in which the test tube 1 is inserted. The tubular portion 4 supports a lower portion of the test tube 1 such that it can be rotated about a central longitudinal axis thereof. Furthermore, the tubular portion 4 holds the test tube 1 in a vertically upright posture. A pair of flange portions 4a and 4b are formed at a lower end portion of the tubular portion 4. The flange portions 4a and 4b are aligned coaxially and spaced apart in an axial direction of the tubular portion 4. A guide groove 4c is formed between the flange portions 4a and 4b. The guide groove 4c has an annular shape which is successive in a peripheral direction of the tubular portion 4.

The holder 3 holding the test tube 1 is transported along a transport path 5. The transport path 5 comprises a belt conveyor 6, and guide rails 7, 8. The belt conveyor 6 transports the test tube 1 held by the holder 3 together with the holder 3. The guide rails 7, 8 are arranged in parallel to each other while the belt conveyor 6 is sandwiched therebetween. The guide rails 7, 8 have guide projections 7a, 8a, respectively. The guide projections 7a, 8a are engaged with the guide groove 4c of the tubular portion 4 so as to slide therein. The engagement allows the holder 3 to be held on the belt conveyor 6 in a vertically upright posture.

The transport path 5 has a correcting position P1 at its middle part. A rotation mechanism 10 is provided at the correcting position P1. The rotation mechanism 10 has a function of rotating the test tube 1 about a central longitudinal axis thereof, and a function of clamping a portion of the test tube 1 which projects over the holder 3 when the test tube 1 held by the holder 3 is transported to the correcting position P1.

As shown in FIG. 1 and FIG. 3, the rotation mechanism 10 comprises a first clamp arm 11, a second clamp arm 12, a pair of drive rollers 13, a pair of follower rollers 14, and a rotary actuator 17. The first clamp arm 11 and the second clamp arm 12 are horizontally provided above the transport path 5. One-side end portions of the first clamp arm 11 and second clamp arm 12 are supported via pivot shafts 11a, 12a, respectively, via an attachment frame 9 which extends upwardly from the guide rail 8. Intermediate gears 15, 16 are coaxially fixed at the pivot shafts 11a, 12a, respectively. The intermediate gears 15, 16 are engaged with each other.

The drive rollers 13 and the follower rollers 14 are examples of rotary members. The follower rollers 14 are supported at the other end of the first clamp arm 11 so as to be easily rotatable. The follower rollers 14 are aligned and spaced apart in a longitudinal direction of the first clamp arm 11. The drive rollers 13 are supported at the other end of the second clamp arm 12 so as to be easily rotatable. The drive rollers 13 are aligned and spaced apart in a longitudinal direction of the second clamp arm 12.

As shown in FIG. 3, the first clamp arm 11 and the second clamp arm 12 are made to pivot between a clamp position and a release position, with the pivot shafts 11a, 12a serving respectively as fulcrums of pivoting. An angle of pivoting of each of the first clamp arm 11 and the second clamp arm 12 is determined at 90 degrees. At the clamp position, the first clamp arm 11 and the second clamp arm 12 advance on the transport path 5 so as to be parallel to each other and face with the test tube 1 transported to the correcting position P1 sandwiched therebetween. Moreover, the drive rollers 13 and the follower rollers 14 are brought into contact with the outer peripheral surface of the upper portion of the test tube 1 to sandwich the upper portion of the test tube 1.

The test tube 1 is thereby stopped temporarily at the correcting position P1. At the release position, the first clamp arm 11 and the second clamp arm 12 retreat in a direction of moving away from the correcting position P1 so as to be parallel to the transport path 5. Thus, holding the test tube 1 by the drive rollers 13 and the follower rollers 14 is released.

As shown in FIG. 1 and FIG. 3, the paired drive rollers 13 have interlocking gears 18a, 18b, respectively. The interlocking gears 18a, 18b are coaxially arranged on the drive rollers 13 and rotated together with the drive rollers 13. The interlocking gears 18a, 18b are spaced apart from each other and engage with a drive gear 18c. The drive gear 18c is rotated in accordance with torque from a motor 19. The motor 18 is supported by the other end of the second clamp arm 12. When the drive gear 18c is rotated, the interlocking gears 18a, 18b are rotated in the same direction as represented by arrows in FIG. 3. The paired drive rollers 13 are thereby rotated in the same direction as the interlocking gears 18a, 18b.

When the first clamp arm 11 and the second clamp arm 12 are at the clamp position, if the drive rollers 13 are rotated via the motor 19 the torque of the drive rollers 13 are transmitted to the test tube 1 sandwiched between the drive rollers 13 and the follower rollers 14. The test tube 1 is thereby rotated about a central longitudinal axis thereof, at the correcting position P1.

The rotary actuator 17 is provided to pivot the first clamp arm 11 and the second clamp arm 12 between the clamp position and the release position. The rotary actuator 17 rotates the intermediate gear 15 interlocking the first clamp arm 11 in a range of angle of 90 degrees such that the intermediate gear 15 can be rotated in a reverse direction. The intermediate gear 16 interlocking the second clamp arm 12 is engaged with the intermediate gear 15. The first clamp arm 11 and the second clamp arm 12 are pivoted in a reverse direction, synchronously with each other.

The rotary actuator 17 may be operated electrically, hydraulically or pneumatically, i.e. any operation scheme is applicable. In the present embodiment, pneumatic rotary actuator 17 whose working pressure can be adjusted is employed to certainly conduct rotating the test tube 1 and clamping the test tube 1 by the single rotation mechanism 10.

Specifically, force of sandwiching the test tube 1 between the drive rollers 13 and the follower rollers 14 is determined on the basis of the working pressure of the rotary actuator 17 to pivot the first clamp arm 11 and the second clamp arm 12. When the test tube 1 is rotated, slide resistance generated at a contact portion between the test tube 1 and the drive rollers 13 and a contact portion between the tube 1 and the follower rollers 14 should preferably be reduced to easily rotate the test tube 1. On the other hand, when rotation of the test tube 1 is stopped and then the test tube 1 is clamped, the test tube 1 should preferably be sandwiched strongly between the drive rollers 13 and the follower rollers 14.

To realize this, the working pressure of the rotary actuator 17 is varied at two stages, i.e. at the time of rotating the test tube 1 and the time of clamping the test tube 1, in the present embodiment. Specifically, when the test tube 1 is rotated, the pneumatic pressure regarded as the working pressure of the rotary actuator 17 is set at about 0.2 MPa. When the test tube 1 is clamped, the pneumatic pressure of the rotary actuator 17 is set at about 0.5 MPa. Therefore, when the test tube 1 is clamped, the drive rollers 13 and the follower rollers 14 sandwich the test tube 1 with greater force than that at the time of rotating the test tube 1.

Figure 4:
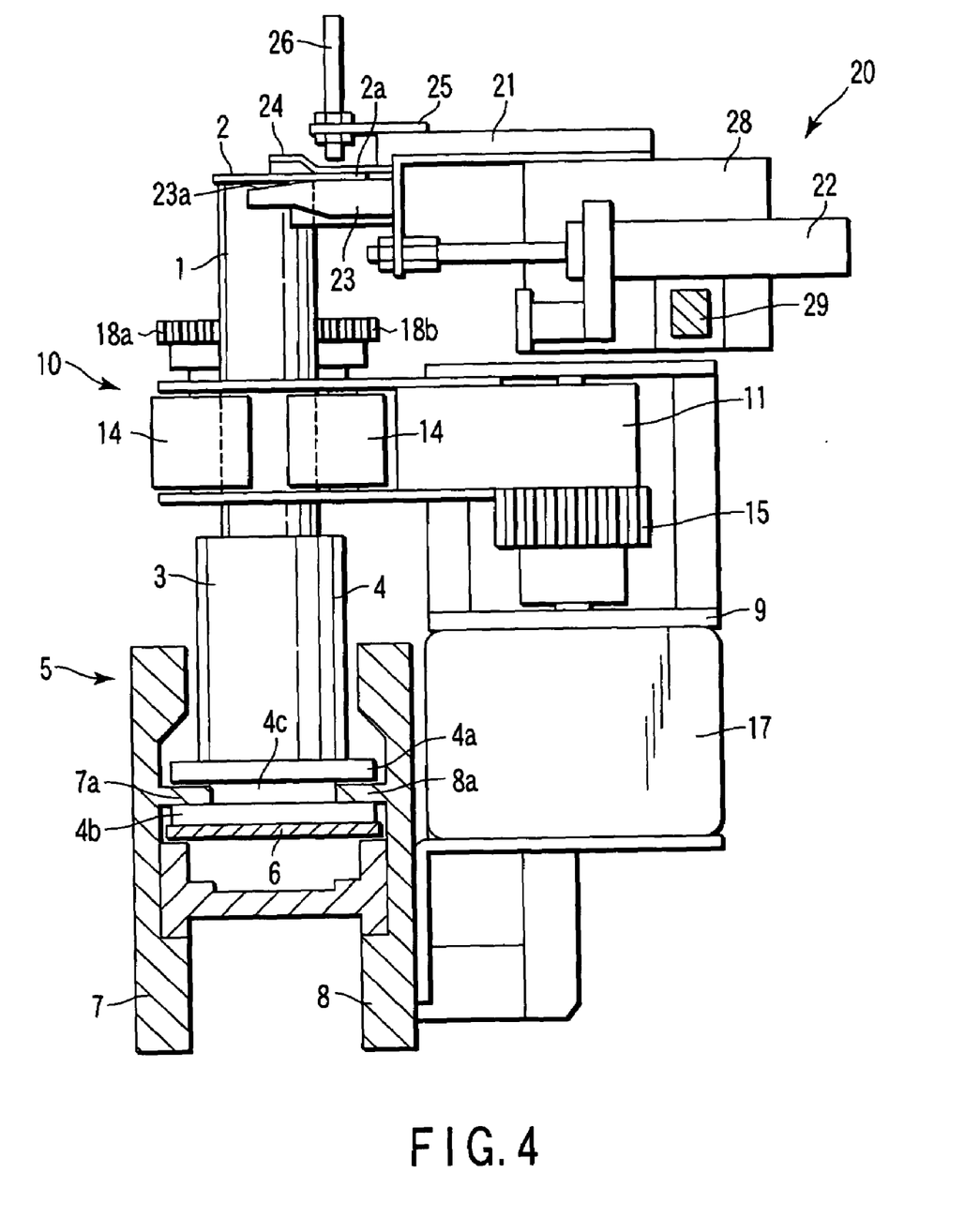
FIG. 4 is a front view of the cap removing apparatus according to the embodiment of the present invention, showing a relationship in position among the test tube held by a holder, a rotation mechanism which rotates the test tube, and the correction mechanism.
Figure 5:
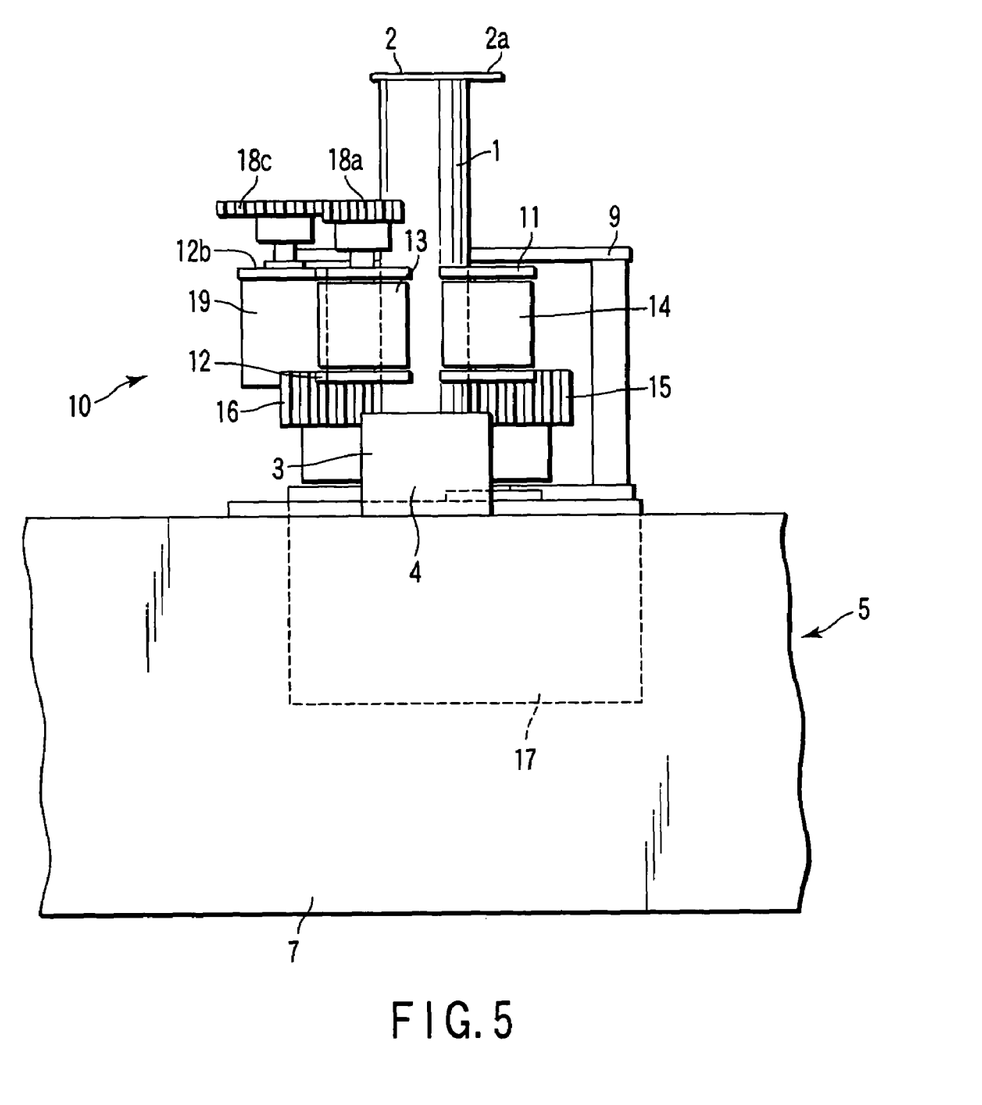
FIG. 5 is a side view of the cap removing apparatus according to the embodiment of the present invention, showing a relationship in position between the test tube held by the holder and the rotation mechanism.

As shown in FIG. 1, FIG. 2 and FIG. 4, a correction mechanism 20 is provided at a middle part of the transport path 5. The correction mechanism 20 corrects the knob portion 2a of the cap 2 of the test tube 1 to a regular posture when the test tube 1 is transported to the correcting position P1. Since the cap 2 is formed of a soft material, the knob portion 2a projecting from the outer peripheral edge of the cap 2 is simply deformed even with a small force. Deformation of the knob portion 2a is classified into four kinds shown in FIG. 6A to FIG. 6D.

Figure 6A:
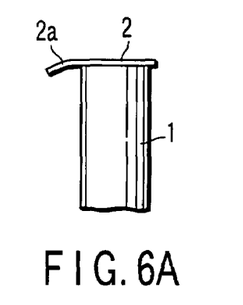
FIG. 6A is a side view of the test tube in the embodiment of the present invention, showing a state of a knob portion of the cap being bent downwardly.
Figure 6B:
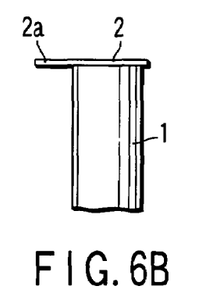
FIG. 6B is a side view of the test tube in the embodiment of the present invention, showing a state of a knob portion of the cap being held in a regular posture.
Figure 6C:
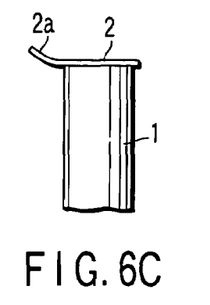
FIG. 6C is a side view of the test tube in the embodiment of the present invention, showing a state of a knob portion of the cap being bent upwardly.
Figure 6D:
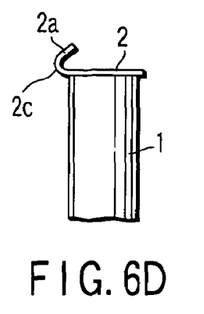
FIG. 6D is a side view of the test tube in the embodiment of the present invention, showing a state of a knob portion of the cap being folded upwardly.
Figure 7A:
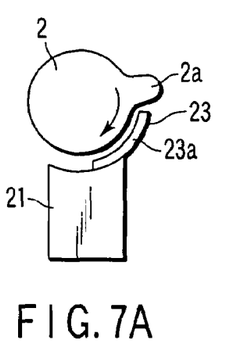
FIG. 7A to FIG. 7D are plan views showing a process in which the downwardly bent knob portion of the cap is corrected via a first correction claw, in a rotating direction of the cap, in the embodiment of the present invention.
Figure 7B:
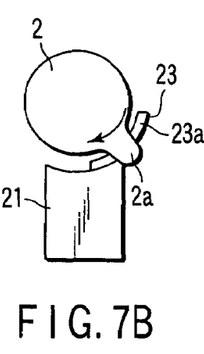
Figure 7C:
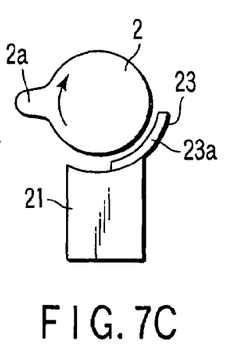
Figure 7D:
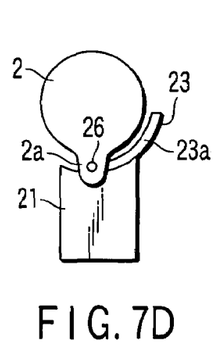
Figure 8A:
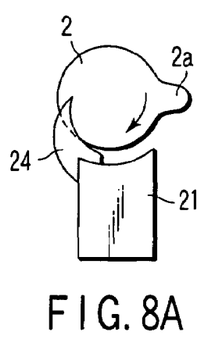
FIG. 8A to FIG. 8D are plan views showing a process in which the upwardly bent knob portion of the cap is corrected via a second correction claw, in a rotating direction of the cap, in the embodiment of the present invention.
Figure 8B:
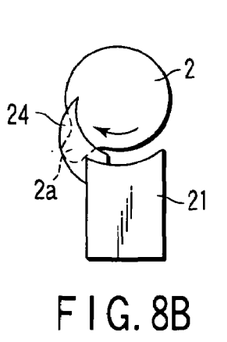
Figure 8C:
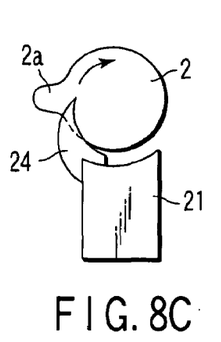
Figure 8D:
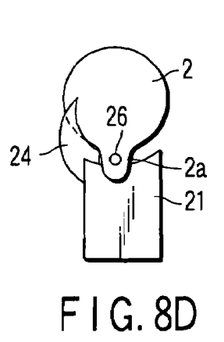

FIG. 6A shows a state of the knob portion 2a being bent downwardly from the outer peripheral edge of the cap 2. FIG. 6B shows a regular state of the knob portion 2a projecting horizontally from the outer peripheral edge of the cap 2. FIG. 6C shows a state of the knob portion 2a being bent upwardly from the outer peripheral edge of the cap 2. FIG. 6D shows the state of the knob portion 2a being folded upwardly.

The correction mechanism 20 corrects the knob portion 2a deformed as shown in, for example, FIG. 6A, FIG. 6C and FIG. 6D to a regular state as shown in FIG. 6B, at the correcting position P1. The correction mechanism 20 comprises a movable body 28, a moving member 21, a first correction claw 23 and a second correction claw 24.

The movable body 28 is supported to be slidable on a guide rail 29. The guide rail 29 is arranged parallel to the transport path 5, at the side of the transport path 5. One of ends of the guide rail 29 is positioned beside the correcting position P1. The movable body 28 can linearly slide between a first slide position and a second slide position. At the first slide position, the movable body 28 advances to a position adjacent to the correcting position P1 as represented by a two-dot-chained line of FIG. 2. At the second slide position, the movable body 28 retreats from the correcting position P1 to a position which is remote to the upstream side along the direction of transporting the test tube 1, as represented by a solid line of FIG. 2. Moreover, the movable body 28 is coupled to a first cylinder 27. The first cylinder 27 slides the movable body 28 between the first slide position and the second slide position.

The moving member 21 is supported on the movable body 28 via a second cylinder 22. The second cylinder 22 moves the moving member 21 linearly between the first position and the second position. At the first position, the moving member 21 advances to the correcting position P1. At the second position, the moving member 21 retreats from the correcting position P1.

As shown in FIG. 3 and FIG. 4, the first correction claw 23 and the second correction claw 24 are supported by the moving member 21. The first correction claw 23 advances onto a locus of rotation drawn by the knob portion 2a, such that the first correction claw 23 is located below the knob portion 2a when the moving member 21 is moved to the first position. The first correction claw 23 has a guide surface 23a which is curved circularly along the peripheral direction of the cap 2 and which is inclined downwardly toward a tip thereof.

The first correction claw 23 corrects the posture of the knob portion 2a which is bent downwardly as shown in FIG. 6A while the test tube 1 is rotated at least one time. In other words, as shown in FIG. 7A to FIG. 7D, the downwardly bent knob portion 2a runs on to the guide surface 23a of the first correction claw 23 in accordance with the rotation of the test tube 1. The knob portion 2a is thereby pushed up by the guide surface 23a. Thus, the knob portion 2a is corrected to the posture which horizontally projects to the outside in the radial direction of the cap 2, such that the knob portion 2a is positioned on the same plane as the cap 2.

The second correction claw 24 advances onto a locus of rotation drawn by the knob portion 2a, such that the second correction claw 24 is located above the knob portion 2a when the moving member 21 is moved to the first position. The second correction claw 24 is curved circularly along the peripheral direction of the cap 2 and is tapered toward a tip thereof.

The second correction claw 24 corrects the posture of the knob portion 2a which is bent upwardly as shown in FIG. 6C or folded upwardly as shown in FIG. 6D, while the test tube 1 is rotated at least one time. In other words, as shown in FIG. 8A to FIG. 8D, the upwardly bent knob portion 2a is pushed from an upper side by the second correction claw 24 in accordance with the rotation of the test tube 1. Thus, the knob portion 2a is corrected to the posture which horizontally projects to the outside in the radial direction of the cap 2, such that the knob portion 2a is positioned on the same plane as the cap 2.

The knob portion 2a which is folded upwardly as shown in FIG. 6D has a folded portion 2c. The second correction claw 24 enters the folded portion 2c of the knob portion 2a and passes through the folded portion 2c in accordance with the rotation of the test tube 1. Then, the folded portion 2c is pushed back by the second correction claw 24 and the knob portion 2a is pushed downwardly. Thus, the upwardly folded knob portion 2a is corrected to the posture which horizontally projects to the outside in the radial direction of the cap 2, such that the knob portion 2a is positioned on the same plane as the cap 2.

As shown in FIG. 3 and FIG. 4, a support arm 25 is attached to the moving member 21. A tip of the support arm 25 projects over the locus of rotation drawn by the knob portion 2a. A monitor sensor 26 is attached to the tip of the support arm 25. The monitor sensor 26 is an example of a detection mechanism which detects the position of the corrected knob portion 2a. The knob portion 2a is positioned below the monitor sensor 26 when the knob portion 2a oriented in a direction orthogonal to the transporting direction of the test tube 1.

The monitor sensor 26 outputs a detection signal to stop the motor 18 when the monitor sensor 26 detects the knob portion 2a. Thus, rotation of the test tube 1 is stopped when the corrected knob portion 2a is oriented in the direction orthogonal to the direction of transporting the test tube 1. Orientation of the knob portion 2a to the test tube 1 is thereby determined.

As shown in FIG. 2, a frame 31 is provided at a position which is displaced from the correcting position P1 to the downstream side along the direction of transporting the test tube 1. The frame 31 is bridged across the transport path 5 and extended over the transport path 5. The frame 31 supports a removing mechanism 30. The removing mechanism 30 is provided to automatically remove the cap 2 from the opening 1a of the test tube 1. The removing mechanism 30 comprises an elevation body 33, a movable body 37, a pivoting body 39 ands a pair of sandwich plates 43, 44.

The elevation body 33 is hung from an upper end of the frame 31 via a cylinder 32. The elevation body 33 is positioned above the transport path 5. The cylinder 32 moves down the elevation body 33 toward the transport path 5 or pulls up elevation body 33 away from the transport path 5.

The movable body 37 is supported by the elevation body 33 via a guide rail 33a and a ball screw 35. The guide rail 33a and the ball screw 35 are extended horizontally to cross the transport path 5, and are arranged parallel to each other and spaced apart. The movable body 37 can horizontally slide so as to cross the transport path 5 with the guide rail 33a and the ball screw 35 serving as guides.

The ball screw 35 rotates by receiving torque from a stepping motor 36. Due to the rotation of the ball screw 35, the movable body 37 is horizontally moved between the first slide position and the second slide position so as to cross the transport path 5. The stepping motor 36 is supported by the elevation body 33 to move up and down together with the elevation body 33. The frame 31 has a longitudinal slot 31a to avoid the stepping motor 36.

The pivoting body 39 is supported by the movable body 37 via a rotary actuator 38. The rotary actuator 38 is an example of a first actuator and has an axis of rotation X which horizontally extends along the direction of transporting the test tube 1. The axis of rotation X horizontally extends along the direction of transporting the test tube 1 so as to be orthogonal to the direction of moving the movable body 37. Thus, the axis of rotation X is orthogonal to the test tube 1 transported along the transport path 5.

As shown in FIG. 1 and FIG. 2, a pair of cylinders 41, 42 are attached to a part which is eccentric from a center of rotation of the pivoting body 39. The cylinders 41, 42 are examples of a second actuator, and are arranged side by side and spaced apart. The cylinders 41, 42 have piston rods 45, 46, respectively. The piston rods 45, 46 project from the cylinders 41, 42, and are arranged parallel to each other and spaced apart.

The sandwich plates 43, 44 are provided to sandwich the knob portion 2a of the cap 2. The sandwich plates 43, 44 are fixed at one-side ends of the piston rods 45, 46, respectively to face each other. The sandwich plates 43, 44 are thereby moved in a direction of moving close to each other or moving away from each other by the operations of the cylinders 41, 42.

The sandwich plates 43, 44 have sandwich surfaces, respectively. Elastic members 43a, 44a are attached to the sandwich surfaces of the sandwich plates 43, 44, respectively. When the knob portion 2a of the cap 2 is sandwiched between the sandwich plates 43, 44, the elastic members 43a, 44a are brought into contact with the knob portion 2a.

Figure 11:
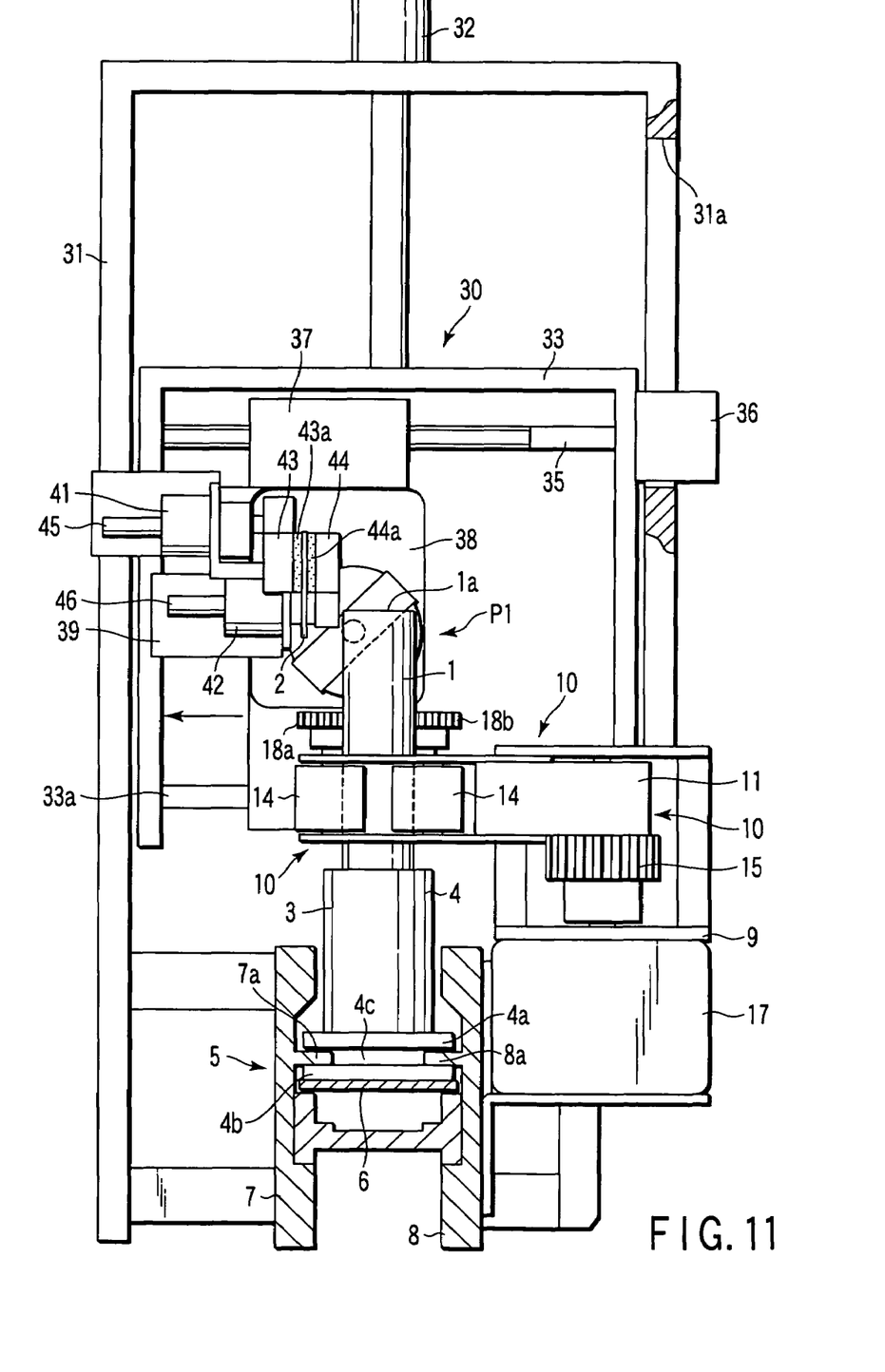
FIG. 11 is a front view of the cap removing apparatus according to the embodiment of the present invention, showing a state in which the cap is removed from the opening of the test tube via the sandwich plates of the removing mechanism.

The rotary actuator 38 pivots the pivoting body 39 in a range of angle of 90 degrees between the first pivot position and the second pivot position, about the axis of rotation X. At the first pivot position, the piston rods 45, 46 of the cylinders 41, 42 are in an upright position and the sandwich plates 43, 44 are opposite to each other in the longitudinal direction as shown in FIG. 1. At the second pivot position, the piston rods 45, 46 of the cylinders 41, 42 are horizontally oriented and the sandwich plates 43, 44 are opposite to each other in the vertical direction as shown in FIG. 11.

The stepping motor 36, the movable body 37, the rotary actuator 38, the pivoting body 39, the cylinders 41, 42, and the sandwich plates 43, 44 are supported by the elevation body 33 as a module. Thus, the cylinder 32 from which the elevation body 33 is hung down allows the sandwich plates 43, 44 to move up and down between a third position and a fourth position. At the third position, the sandwich plates 43, 44 are moved down to advance to the correcting position P1. At the fourth position, the sandwich plates 43, 44 are moved up to move away from the correcting position P1.

Figure 9:
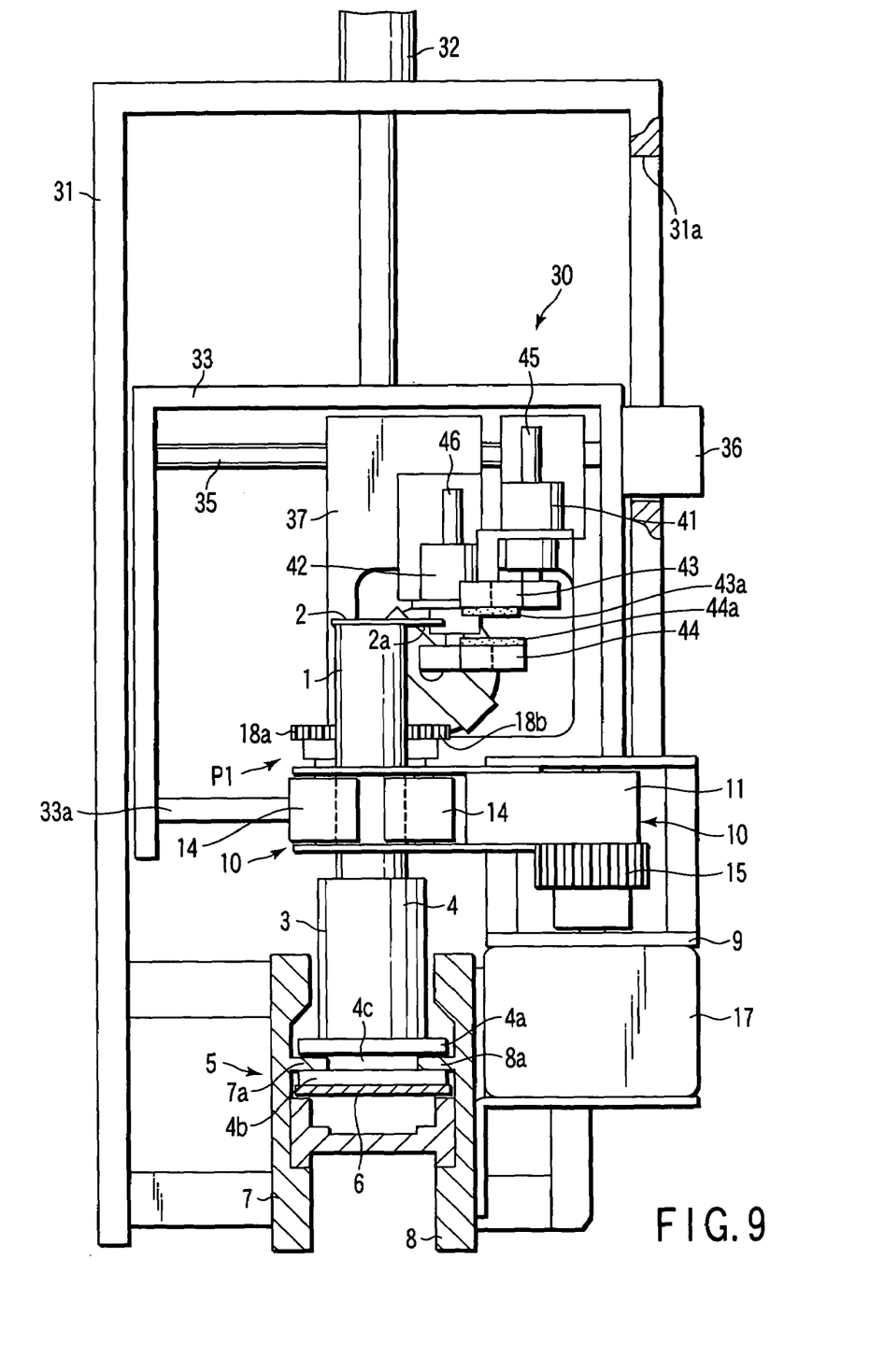
FIG. 9 is a front view of the cap removing apparatus according to the embodiment of the present invention, showing a state in which sandwich plates of the removing mechanism are opposite to the knob portion of the cap.

FIG. 9 shows a state in which the elevation body 33 is moved down by the operation of the cylinder 32 and the sandwich plates 43, 44 of the removing mechanism 30 reach the third position. The movable body 37 is at the first slide position and the pivoting body 39 is at the first pivot position. When the elevation body 33 is moved down, correcting the knob portion 2a by the correction mechanism 20 has been ended. For this reason, the rotation mechanism 10 clamps the upper portion of the test tube 1.

When the movable body 37 is slid at a predetermined stroke from the first slide position to the second slide position by the operation of the stepping motor 36, the corrected knob portion 2a of the cap 2 advances between the elastic member 43a of the sandwich plate 43 and the elastic member 44a of the sandwich plate 44.

Figure 10:
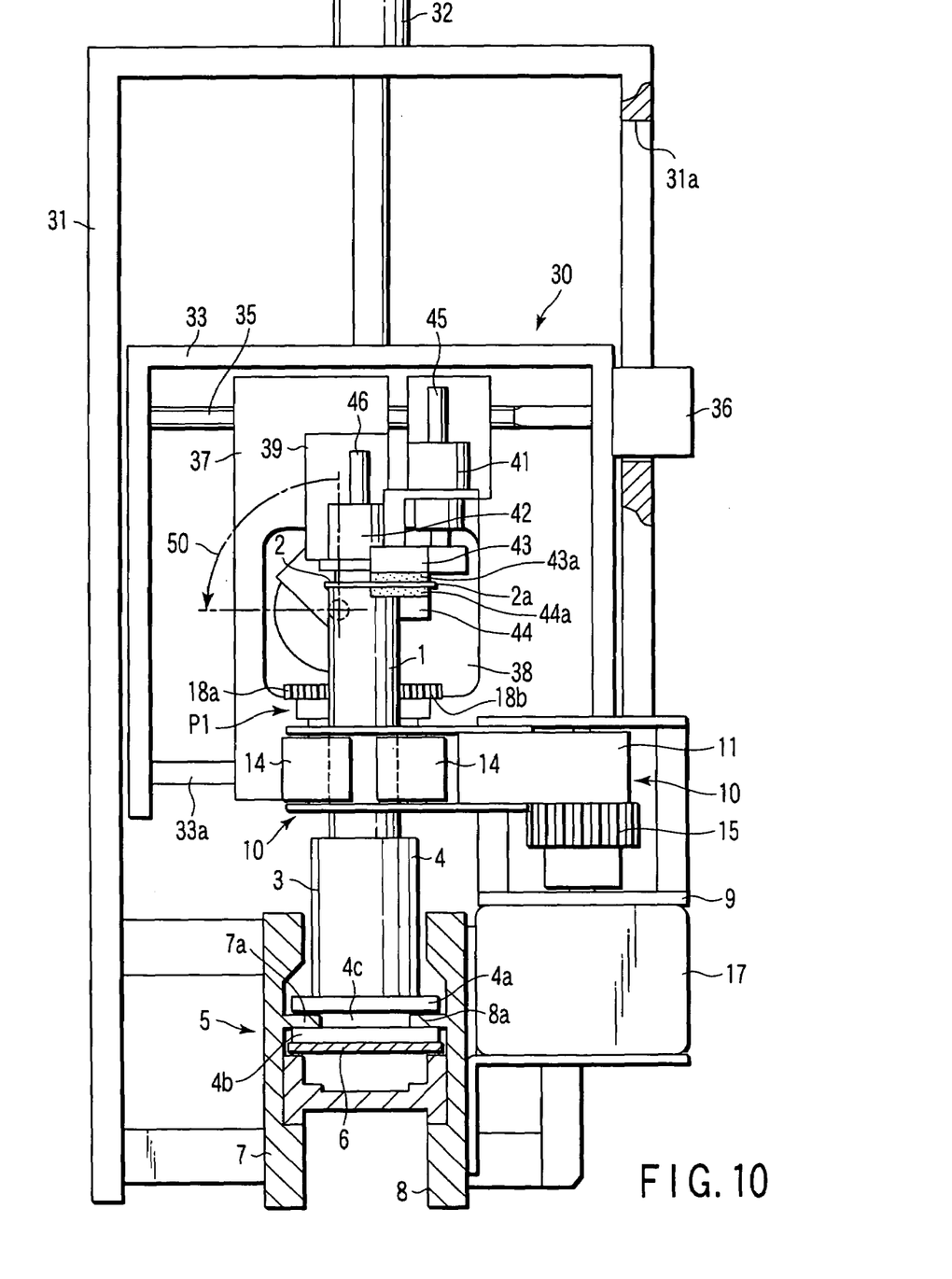
FIG. 10 is a front view of the cap removing apparatus according to the embodiment of the present invention, showing a state in which the sandwich plates of the removing mechanism are sandwiching the knob portion of the cap.

The cylinders 41, 42 are operated after the knob portion 2a advances between the elastic members 43a, 44a. The sandwich plates 43, 44 are moved in the direction of coming close to each other due to the operation of the cylinders 41, 42. As a result, the elastic members 43a, 44a of the sandwich plates 43, 44 sandwich the knob portion 2a of the cap 2 as shown in FIG. 10.

The rotary actuator 38 is operated after the knob portion 2a is sandwiched between the sandwich plates 43, 44. The pivoting body 39 pivots at 90 degrees from the first pivot position to the second pivot position as represented by an arrow 50 in FIG. 10, by the operation of the rotary actuator 38. As a result, the knob portion 2a sandwiched between the sandwich plates 43, 44 is twisted at 90 degrees toward the top of the test tube 1 as shown in FIG. 11. Thus, the cap 2 is removed from the opening 1a of the test tube 1.

After the cap 2 is removed from the test tube 1, the movable body 37 is slid to the second slide position by the operation of the stepping motor 36. The movable body 37 is stopped when the movable body 37 is positioned right above a recovery box 49 provided beside the transport path 5.

The rotary actuator 17 is operated synchronously with the sliding operation of the movable body 37. The first clamp arm 11 and the second clamp arm 12 thereby pivot from the clamp position to the release position, such that clamping the upper portion of the test tube 1 by the drive rollers 13 and the follower rollers 14 is released. As a result, the test tube 1 from which the cap 2 has been removed is transported to a next processing position by the belt conveyor 6.

Figure 12:
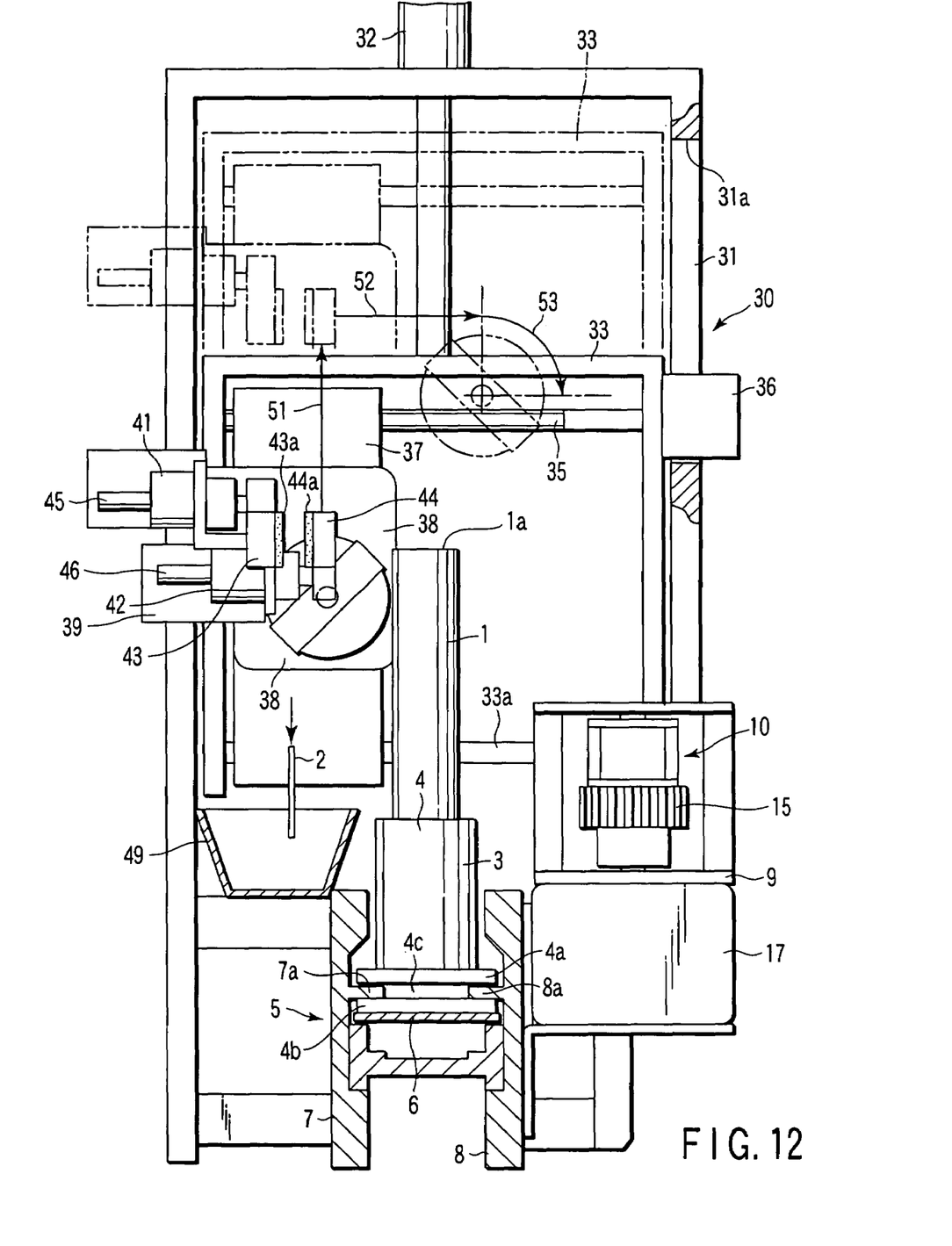
FIG. 12 is a front view of the cap removing apparatus according to the embodiment of the present invention, showing a state in which the sandwich plates of the removing mechanism are stopped above a recovery box.

As shown in FIG. 12, the sandwich plates 43, 44 are moved away from each other by the operation of the cylinders 41, 42 when the movable body 37 is stopped just above the recovery box 49. Due to this movement, sandwiching the knob portion 2a between the elastic members 43a, 44a is released. Thus, the cap 2 removed from the test tube 1 is dropped into the recovery box 49.

When the cap 2 is dropped into the recovery box 49, the elevation body 33 is moved up as represented by an arrow 51 in FIG. 12, by the operation of the cylinder 32. Simultaneously, the movable body 37 is slid from the second slide position to the first slide position as represented by an arrow 52 in FIG. 12, by the operation of the stepping motor 36. Moreover, the pivoting body 39 is pivoted at 90 degrees from the second pivot position to the first pivot position as represented by an arrow 53 in FIG. 12, by the operation of the rotary actuator 38, and returns to the state shown in FIG. 1 to remove a cap 2 from a test tube 1 to be transported next.

According to the apparatus having the above described structure, correction of the knob portion 2a of the cap 2 and removal of the corrected knob portion 2a can be successively conducted at the correcting position P1 fixed at the middle part of the transport path 5. For this reason, the knob portion 2a of the cap 2 can be certainly sandwiched between the sandwich plates 43, 44 and the cap 2 can be quickly removed from the opening 1a of the test tube 1.

The test tube 1 is stopped at the correcting position P1 during the period after correction of the knob portion 2a is ended and before removal of the cap 2 is completed. In other words, the test tube 1 at which correction of the knob portion 2a has been completed does not need to be moved along the transport path 5. Thus, the transport path 5 can be shortened and the apparatus can be made compact. In addition, vibration to rotate the test tube 1 cannot be applied to the test tube 1 after the knob portion 2a is corrected. Therefore, orientation of the corrected knob portion 2a can be constantly maintained and the knob portion 2a can be certainly sandwiched between the sandwich plates 43, 44.

In the above-described structure, when the cap 2 is removed from the test tube 1, the upper portion of the test tube 1 is clamped by using the rotation mechanism 10 which rotates the test tube 1. For this reason, rotating the test tube 1 and clamping the test tube 1 can be conducted with the single rotation mechanism 10, and a mechanism provided only to clamp the test tube 1 can be omitted.

Furthermore, the removing mechanism 30 provided to remove the cap 2 from the test tube 1 advances to the correcting position P1 after the correction mechanism 20 provided to correct the knob portion 2a of the cap 2 retreats from the correcting position P1. For this reason, although correcting the knob portion 2a and removing the cap 2 are conducted at the correcting position P1, the correction mechanism 20 and the removing mechanism 30 do not interfere with each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cap removing apparatus comprising:
   a holder which holds a tube-like container having a central longitudinal axis and an opening blocked by a cap, the cap having a knob portion at an outer peripheral edge thereof;
   a transport path in which the container held by the holder is transported together with the holder, the transport path having a correcting position at a middle part thereof;
   a rotation mechanism provided at the correcting position to rotate the container about said longitudinal axis when the container is transported to the correcting position;

a correction mechanism which corrects a posture of the knob portion of the cap when the container is being rotated by the rotation mechanism; and a removing mechanism which grasps the knob portion of the cap corrected by the correction mechanism and removes the cap from the container, wherein the correction mechanism is configured to move between a first position at which the correction mechanism advances to the correcting position to correct the posture of the knob portion and a second position at which the correction mechanism retreats from the correcting position, the removing mechanism is configured to move between a third position at which the removing mechanism advances to the correcting position to remove the cap from the container and a fourth position at which the removing mechanism retreats from the correcting position, and the removing mechanism is moved to the third position when the correction mechanism retreats to the second position.

2. The cap removing apparatus according to claim 1, wherein the rotation mechanism comprises:

a pair of clamp arms capable of moving between a clamp position at which the clamp arms face while sandwiching the container and a release position at which the clamp arms are separated from the container;

an actuator which moves the clamp arms to the clamp position and the release position; and rotary members provided at the clamp arms, respectively, to sandwich and rotate the container when the clamp arms are moved to the clamp position.

3. The cap removing apparatus according to claim 2, wherein the rotation mechanism stops the rotation of the rotary members and holds the container at the correcting position when the removing mechanism removes the cap from the container.

4. The cap removing apparatus according to claim 3, wherein the actuator has an actuating force to move the clamp arms to the clamp position, the actuating force is adjustable at two stages, and the actuating force of the actuator to rotate the container via the rotary members is smaller than the actuating force of the actuator to stop the rotation of the rotary members and hold the container.

5. The cap removing apparatus according to claim 4, wherein when the rotary members hold the container, the rotary members sandwich the container with a force greater than a force to rotate the container.

6. The cap removing apparatus according to claim 1, wherein the correction mechanism has first and second correction claws which advance in a locus of rotation drawn by the knob portion of the cap when the correction mechanism is moved to the first position, and the first and second correction claws correct the posture of the knob portion such that the knob portion and the cap are positioned in one plane when the first and second correction claws are opposite to the knob portion of the cap in accordance with the rotation of the container.

7. The cap removing apparatus according to claim 6, wherein the correction mechanism includes a detection mechanism which detects that the knob portion corrected by the first and second correction claws reaches a position where the cap is to be removed, and the detection mechanism outputs a detection signal to stop the rotation of the container to the rotation mechanism when the detection mechanism detects the position of the knob portion.

8. The cap removing apparatus according to claim 1, wherein the removing mechanism includes:

a pair of sandwich plates which sandwich the knob portion;

a first actuator which pivots the sandwich plates around an axis orthogonal to the container; and second actuators which move the sandwich plates in a direction of moving close to each other or moving away from each other, and the removing mechanism removes the cap from the opening of the container by pivoting the sandwich plates sandwiching the knob portion via the first actuator.

9. The cap removing apparatus according to claim 8, wherein the removing mechanism has a movable body which supports the sandwich plates and the first and second actuators, and the movable body is configured to move between a first slide position where the sandwich plates are moved close to the opening of the container and a second slide position where the sandwich plates are moved away from the first slide position to a side of the container.

* * * * *